US00PP16012P2

(12) United States Plant Patent
Olesen et al.

(10) Patent No.: US PP16,012 P2
(45) Date of Patent: Sep. 27, 2005

(54) ***CLEMATIS* PLANT NAMED 'EVIPO020'**

(50) Latin Name: *Clematis flammula viticella*
Varietal Denomination: Evipo020

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 50 days.

(21) Appl. No.: 10/817,362

(22) Filed: Apr. 1, 2004

(51) Int. Cl.[7] ..... A01H 5/00
(52) U.S. Cl. ..... Plt./228
(58) Field of Search ..... Plt./228

*Primary Examiner*—Anne Marie Grunberg
*Assistant Examiner*—Annette H Para

(57) ABSTRACT

A new *Clematis* cultivar which is well suited to propagation in glasshouses, with a tall growth habit, profuse, purple flowers, and continuous summer flowering. The variety successfully propagates from softwood cuttings and is suitable for cultivation in commercial glasshouses. This new and distinct variety has shown to be uniform and stable in the resulting generations from propagation.

2 Drawing Sheets

Botanical classification: Genus—*Clematis*. Subgenus—*flammula*. Section—*viticella*.
Variety denomination: 'Evipo020'.

SUMMARY OF THE INVENTION

The present invention constitutes a new and distinct variety of *Clematis* which originated from a controlled crossing between the female seed parent, *Clematis viticella* 'Venosa Violacea', a non-patented variety, and the male parent, an un-named seedling.

The new *Clematis* may be distinguished from its female seed parent, 'Venosa Violacea', by the following combination of characteristics:

1. The seed parent has single flowers, while 'Evipo020' has double flowers.
2. The seed parent has more white coloration of the tepals than 'Evipo020'.

The new *Clematis* may be distinguished from its male pollen parent by the following combination of characteristics:

1. The pollen parent variety has fewer tepals per flower than 'Evipo020'.
2. 'Evipo020' has a darker flower color than the pollen parent.

The two parents were crossed and the resulting seed was planted in a controlled environment. The new variety is named 'Evipo020'. The objective of the hybridization of this *Clematis* variety for commercial glasshouse and nursery culture was to create a new and distinct variety with unique qualities that this variety has:

1. Very long flowering season;
2. Purple, double blooms,
3. Substantially improved flower longevity;
4. Improved continuous flowering habit.

These qualities required improvement in *clematis* varieties that were in commercial cultivation and the objectives have been substantially achieved in the new variety, as evidenced by the unique combination of characteristics that are present in 'Evipo020' which distinguish it from all other varieties of which we are aware.

The seeds from the aforementioned hybridization were germinated and evaluations of the resulting seedling plants were conducted in a controlled environment. As a result, 'Evipo020' was selected by Raymond J. Evison and Mogens N. Olesen in their *Clematis* development program in Guernsey, Channel Islands, in July 2000.

Asexual reproduction of 'Evipo020' by cuttings was first done by Raymond J. Evison and Mogens N. Olesen in Domarie Vineries Les Sauvagees, St. Sampsons, Guernsey, Channel Islands, United Kingdom in July 2000. This initial and subsequent propagations have demonstrated that the characteristics of 'Evipo020' are true to type and are transmitted from one generation to the next.

BRIEF DESCRIPTION OF THE DRAWING

The accompanying color illustration show as true as is reasonably possible to obtain in color photographs of this type. Specifically illustrated in FIG. 1:

FIG. 1.2 Mature leaves attached to stem;

FIG. 1.3 Flower at ¼ opening;

FIG. 1.4 Flower bud showing attachment to peduncle and leaflets;

FIG. 1.5 Open flower at various stages of development;

FIG. 1.6 Open flower, underside.

Figure 2:
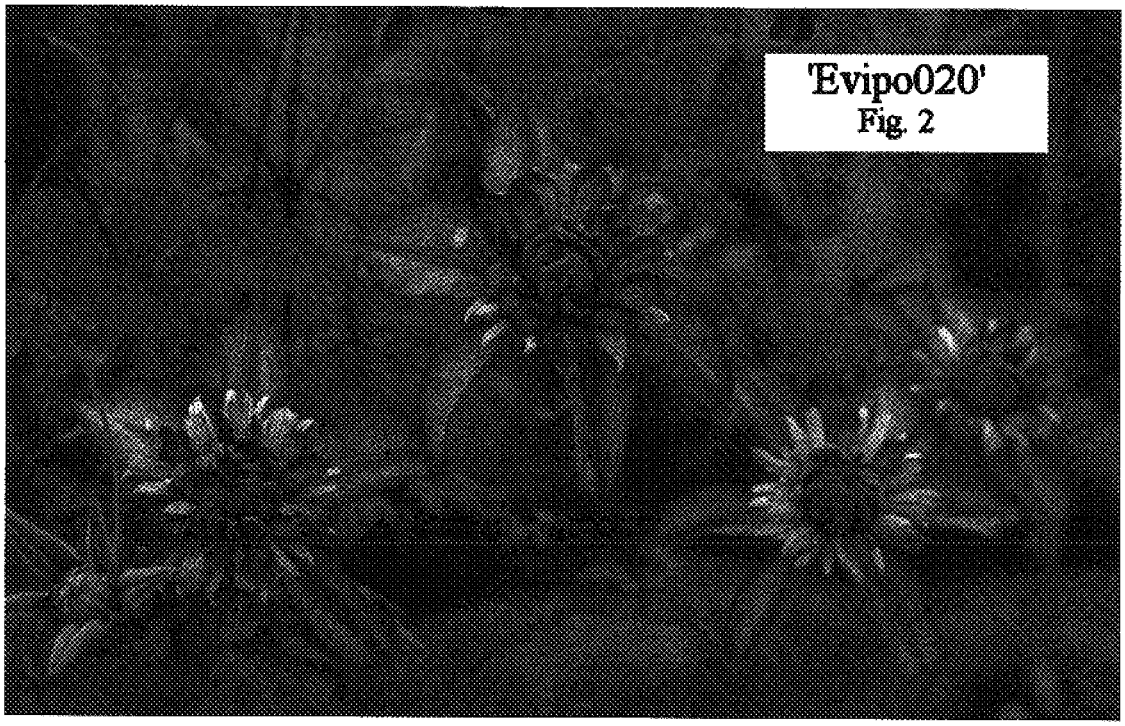

Specifically illustrated in FIG. 2 are open flowers attached to the plant, showing flower detail and attitude.

DETAILED DESCRIPTION OF THE VARIETY

The following is a detailed description of 'Evipo020', as observed in its growth throughout the flowering period in glasshouses in Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'Vyvyan Pennell', a non-patented variety. Chart 1 details several physical characteristics of the 'Evipo020' and 'Vyvyan Pennell'.

CHART 1

| | 'Evipo020' | 'Vyvyan Pennell' |
|---|---|---|
| Tepal Color After Opening | Purple Group 79C | Purple Group 78B |
| Flower Diameter | 80 to 90 mm | 150 to 180 mm |
| Flowering habit | Continuous | Recurrent |

FLOWER AND FLOWER BUD

Blooming habit: Continuous. Flowering occurs on new growth.

Flower bud:

*Size.*—20 to 30 mm in length. Bud diameter is 12 mm on average.

*Bud form.*—Short Ovoid.

*Bud color.*—Red-Purple Group 59A at ¼ opening.

Peduncle:

*Surface.*—Smooth.

*Length.*—90–120 mm average length.

*Color.*—Red-Purple Group 59A.

*Aspect.*—Horizontal.

Receptacle: None.

Flower arrangement:

*Borne.*—Flowers occur along the stem at each leaf axil, on new growth.

Flower bloom.

*Size.*—80–90 mm in diameter. Tepals themselves contribute very little to flower depth, as they open to a flat plane. However, flower depth is achieved by the protrusion of reproductive parts, 25 to 30 mm on average.

*Profile.*—Upon opening, flowers are cupped. After opening flowers are globular with sepals normally straight and occasionally reflexing.

*Color.*—Upon opening: Upper surface is Purple Group 77A. The reverse side is Purple Group N77D. After opening: Upper and lower surfaces are Purple Group 79C. Intonations of White Group N155B observed on both surfaces.

*Variations.*—As the tepals age flower color exhibits more violet blue tones.

*Fragrance.*—None.

*Lasting quality.*—On the plant flowers typically remain for a duration of 4 weeks. As a cut flower flowers typically have a vase life of 10 days.

Tepals:

*Quantity.*—There are 6 outer tepals. Flowers produce a central dome of 100 petaloid stamens.

*Shape.*—Individual tepal shape is elliptic. Tepal base and apecies are acute.

*Cross section.*—Flat to bi-laterally reflexed.

*Margins.*—Entire. Weak undulations observed.

*Recurvature of tip.*—Outer tepals occasionally recurved.

*Persistence.*—Outer tepals wither while inner tepals persist.

*Arrangement.*—Tepals are arranged regularly.

Reproductive organs: None. Flowers are completely sterile.

PLANT

Plant form: Climbing and spreading.

Plant growth: Average vigor. Seasons growth attains 2–3 meters in height. Plants generally spread 1 meter when trellised.

Hardiness: Trials to date show the variety hardy in USDA Zones 6–9.

Stems:

*Color.*—Young wood: Green Group 137D. Other intonations of Red-Purple Group 59A observed. Older wood: Greyed-Orange Group 165C.

*Internodes.*—Shape: Cylindrical. Length: 130 to 180 mm.

*Surface texture.*—Young wood: Smooth. Older wood: Smooth.

Plant foliage:

*Characteristics.*—Evergreen.

*Mature leaf form.*—Trifoliate. Compound leaves consist of 5 leaflets on average.

*Compound leaf size:* 115 to 250 mm in length. Width is generally 100 to 130 mm.

*Color.*—Upper surfaces of mature leaves are Green Group 137A. Lower surfaces are Green Group 137C. Upper surfaces of new leaves are Green Group 137C. Lower surfaces are Green Group 137A.

Plant leaves and leaflets:

*Petiole length.*—30 to 60 mm.

*Leaflet margin.*—Leaflets have margins which are entire.

*Leaflet shape.*—Base: Acute to Rounded. Apex: Acute.

*Leaflet size.*—40 mm (l)×25 mm (w).

*Texture.*—Thin.

*Surface.*—Matte Finish.

Disease resistance: Subject to any disease that normally attacks the species.

We claim:

1. A new and distinct variety of *Clematis* plant named 'Evipo020', herein described and illustrated as a distinct and novel *Clematis* variety due to its abundant purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

Figure 1:
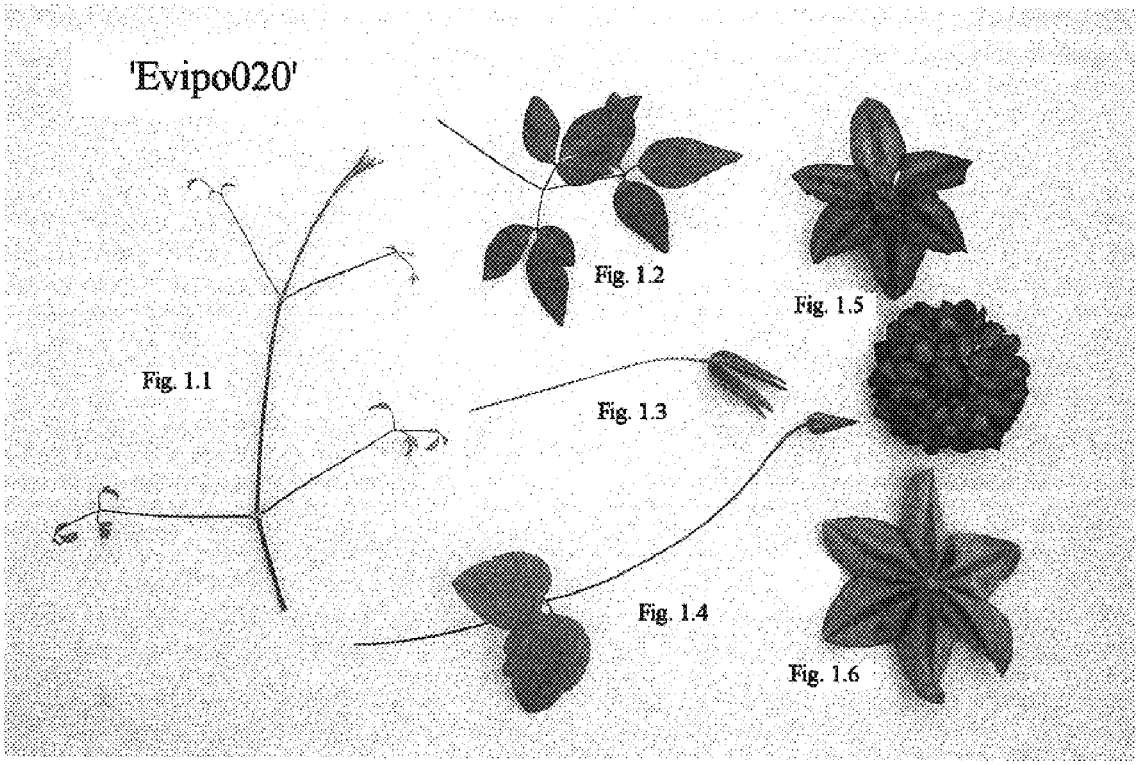
FIG. 1.1 Juvenile stem with juvenile foliage.

'Evipo020'
Fig. 1.1
Fig. 1.2
Fig. 1.3
Fig. 1.4
Fig. 1.5
Fig. 1.6

'Evipo020'